US006738091B1

United States Patent
Eouzan et al.

(10) Patent No.: US 6,738,091 B1
(45) Date of Patent: May 18, 2004

(54) DIGITAL CAMERA AND METHOD OF CONTROL USING PRE-SET DIGITAL SETTING FUNCTIONS AND OPTIONS

(75) Inventors: Jean-Yves Eouzan, Cesson Sevigne (FR); Christophe Barnaud, Versailles (FR)

(73) Assignee: Thomson-CSF, Paris (FR)

( * ) Notice: Subject to any disclaimer, the term of this patent is extended or adjusted under 35 U.S.C. 154(b) by 0 days.

(21) Appl. No.: 09/460,423

(22) Filed: Dec. 14, 1999

(30) Foreign Application Priority Data

Dec. 15, 1998 (FR) .............................. 98 15832

(51) Int. Cl.⁷ ........................ H04N 5/232; H04N 7/18
(52) U.S. Cl. ............... 348/211.14; 348/65; 348/333.02
(58) Field of Search ............... 348/65, 71–76, 348/135, 143, 207.99, 211.14, 222.1, 333.01, 333.02, 333.11, 333.12; 600/118

(56) References Cited

U.S. PATENT DOCUMENTS

| | | | |
|---|---|---|---|
| 4,472,740 A | * 9/1984 | Doi .............................. | 348/361 |
| 4,488,305 A | 12/1984 | Claverie et al. | |
| 4,528,595 A | 7/1985 | Eouzan | |
| 4,562,471 A | 12/1985 | Eouzan et al. | |
| 4,845,382 A | 7/1989 | Eouzan et al. | |
| 5,091,773 A | 2/1992 | Fouche et al. | |
| 5,231,481 A | 7/1993 | Eouzan et al. | |
| 5,262,852 A | 11/1993 | Eouzan et al. | |
| 5,365,270 A | 11/1994 | Guichard et al. | |
| 5,894,322 A | * 4/1999 | Hamano ....................... | 348/68 |
| 5,999,213 A | * 12/1999 | Tsushima ..................... | 348/180 |
| 6,120,435 A | * 9/2000 | Eino ............................. | 348/65 |
| 6,414,714 B1 | * 7/2002 | Kurashige .............. | 348/207.99 |

FOREIGN PATENT DOCUMENTS

| | | |
|---|---|---|
| EP | 0 534 198 | 3/1993 |
| EP | 0 664 475 | 7/1995 |
| EP | 0 748 132 | 12/1996 |
| JP | 8-116529 | 5/1996 |

OTHER PUBLICATIONS

Laurence J. Thorpe, et al., "The All–Digital Camcorder– The Arrival of Electronic Cinematography", SMPTE Journal, vol. 105, No. 1, Jan. 1, 1996, pp. 13–30.
Patent Abstracts of Japan, vol. 016, No. 110 (C–0920), Mar. 18, 1992, JP 03 284230, Dec. 13, 1991.
Patent Abstracts of Japan, vol. 1996, No. 03, Mar. 29, 1996, JP 07 303596, Nov. 21, 1995.

* cited by examiner

Primary Examiner—Ngoc-Yen Vu
(74) Attorney, Agent, or Firm—Oblon, Spivak, McClelland, Maier & Neustadt, P.C.

(57) ABSTRACT

Disclosed are a digital display camera in a changing environment and an associated method of digital control. The method can be applied more particularly to digital cameras for endoscopy. It enables a user to access a very large number of parameters of settings while at the same time using only a limited number of data inputs. The camera is constituted by an optoelectrical detection head (DH) and a processing unit (PU) connected to the detection head. The processing unit is provided with a keyboard (FFK) and is connected to a remote control unit (RC). The processing unit (PU) contains pre-recorded digital functions, each enabling the setting of at least one parameter of the camera, as well as options that are characteristic of a given environment, grouping together a set of said functions. It furthermore comprises especially a module for the monitoring of the data elements entered by the user, for example by means of the keyboard (FFK) or the remote control unit, these data elements representing the functions and/or options chosen, a module for the processing of the data elements corresponding directly to functions and/or options chosen by the user in order to carry out the corresponding settings of the camera.

19 Claims, 3 Drawing Sheets

FIG.2

| SETTING FUNCTIONS | DIRECT ACCESS |
|---|---|
| LUMINOSITY: MANUAL MANAGEMENT OF GAIN | PARTLY |
| LUMINOSITY: MANAGEMENT OF ATTENUATION OF WHITE LEVELS | — |
| LUMINOSITY: AUTOMATIC BLACK LEVEL MANAGEMENT | — |
| LUMINOSITY: MANAGEMENT OF THE BLACK STRETCH/PRESS | — |
| LUMINOSITY: MANAGEMENT OF THE GAMMA | — |
| LUMINOSITY: MANAGEMENT OF THE AGC | PARTLY |
| COLORIMETRY: AUTOMATIC BALANCE OF THE BLACK LEVELS | — |
| COLORIMETRY: AUTOMATIC BALANCE OF THE WHITE LEVELS | YES |
| COLORIMETRY: MATRIX SETTING OF THE COLORS | — |
| COLORIMETRY: MANUAL BALANCING OF THE WHITE LEVELS | YES |
| QUALITY: SHARPENING OF CONTOUR | — |
| QUALITY: PIXEL CORRECTION | — |
| QUALITY: BLACK SHADING | — |
| QUALITY: WHITE SHADING | — |
| QUALITY: FLARE | — |

FIG.3

| MENUS | |
|---|---|
| | CONFIGURATIONS |
| CONFIGURATION: | STANDARD /1/.../7 |
| | OPTIONS |
| APPLICATION: | ABDOMINAL / THORACIC / NEUROSURGERY / ARTHROSCOPY / RETRO-PERITONEAL / CONTACT |
| ENDOSCOPE: | 10mm / 5mm / 3mm / FIBROSCOPE |
| CONTOUR: | --/-/+/++ |
| GAIN: | --/-/+/++ |
| SOURCE: | XENON / HALOGEN |
| AMBIENCE: | NORMAL / HEMORRHAGIC / HYDRIC / FAT |
| LANGUAGE: | FRENCH / ENGLISH / GERMAN / SPANISH |

DIGITAL CAMERA AND METHOD OF CONTROL USING PRE-SET DIGITAL SETTING FUNCTIONS AND OPTIONS

BACKGROUND OF THE INVENTION

1. Field of the Invention

The invention relates to a digital display camera in a changing environment and an associated method of digital control. It can be applied essentially to cameras moving in a biomedical environment. More specifically, the invention relates to the control of endoscopic color cameras used in hospitals to carry out medical or surgical operations using endoscopy.

2. Description of the Prior Art

Endoscopic cameras are usually constituted by an optoelectrical detection head connected to an endoscope and connected to a control unit, the endoscope being introduced into a patient's body. A light source, also connected to the endoscope, provides the necessary illumination to observe the scene. The camera provides a color video image to one or more screens located in the operating theater. By means of setting buttons on the front face of the control unit and/or directly on the detection head of the camera, a doctor can access the settings of some parameters of the camera, for example the gain and the balance of the white levels. These settings are done in an analog way and are limited in number, enabling adaptation in varying degrees to the conditions in which the camera is moving.

However, in a changing medium like that of the human body in which there is a multitude of situations in which the surgeon may operating (such as cavities, nature of the tissues, environment, etc.) these settings are quite insufficient to optimize the quality of the image and work under the most efficient conditions. Now it is not possible to give the doctor access to the largest number of parameters. Firstly, he or she is not necessarily a technical specialist in the subject of cameras and therefore does not have full mastery of the influence of each of the parameters. Secondly, playing on a large number of parameters entails the great risk of ultimately putting the camera out of order and not being able to return to the desired configuration.

To overcome this drawback, the present invention proposes to connect the head of the camera to a digital processing cabinet or unit, said processing unit controlling for example one or more screens and at least one keyboard (for example a keyboard located on the front face of the processing unit and a remote control unit). By means of functions pre-recorded in the control unit each enabling the digital setting of a given number of parameters of the camera, the physician, by means of the method of the invention, can access a very large number of parameters while at the same time using only a limited number of input data elements.

SUMMARY OF THE INVENTION

More specifically, the invention relates to a method for the digital control of a display camera in a changing environment, the camera comprising a plurality of setting parameters and being constituted especially by an optoelectrical detection head and a processing unit connected to the detection head, the method comprising:

a preliminary learning phase enabling the programming of a pre-set number of digital setting functions recorded in the processing unit, each function enabling the setting of at least one parameter of the camera, as well as a predetermined number of options that are characteristic, inter alia, of a given environment, grouping together a set of said functions, these functions being accessible to a user, either directly or in the form of the options, when the processing unit is powered on by the user,
 a step to initialize the camera enabling especially the setting of the parameters of the camera in a standard configuration,
 the monitoring of the data elements entered by the user, these data elements representing the functions and/or options chosen by the user,
 the processing of the data elements corresponding directly to setting functions or options chosen by the user in order to carry out the corresponding settings of the camera.

The invention also relates to a digital camera implementing the method according to the invention.

Advantageously, the method according to the invention furthermore comprises a system of customized configuration management enabling the user, during the choice of one or more options forming a customized configuration, to record this configuration. Thus the user, with a minimum number of controls, can obtain settings suited to the environment in which the camera is operating, very easily change a configuration and return, if need be, to a standard configuration. The method according to the invention thus makes it possible to obtain an appreciably better quality of images without increasing the complexity of use of the camera.

BRIEF DESCRIPTION OF THE DRAWINGS

Other characteristics and advantages of the invention shall appear from the following description, illustrated by the appended figures, of which:

FIG. 2 is a list giving examples of pre-recorded setting functions;

FIG. 3 is a list giving examples of pre-recorded options;

MORE DETAILED DESCRIPTION

In these figures, equivalent elements bear identical references.

Figure 1:
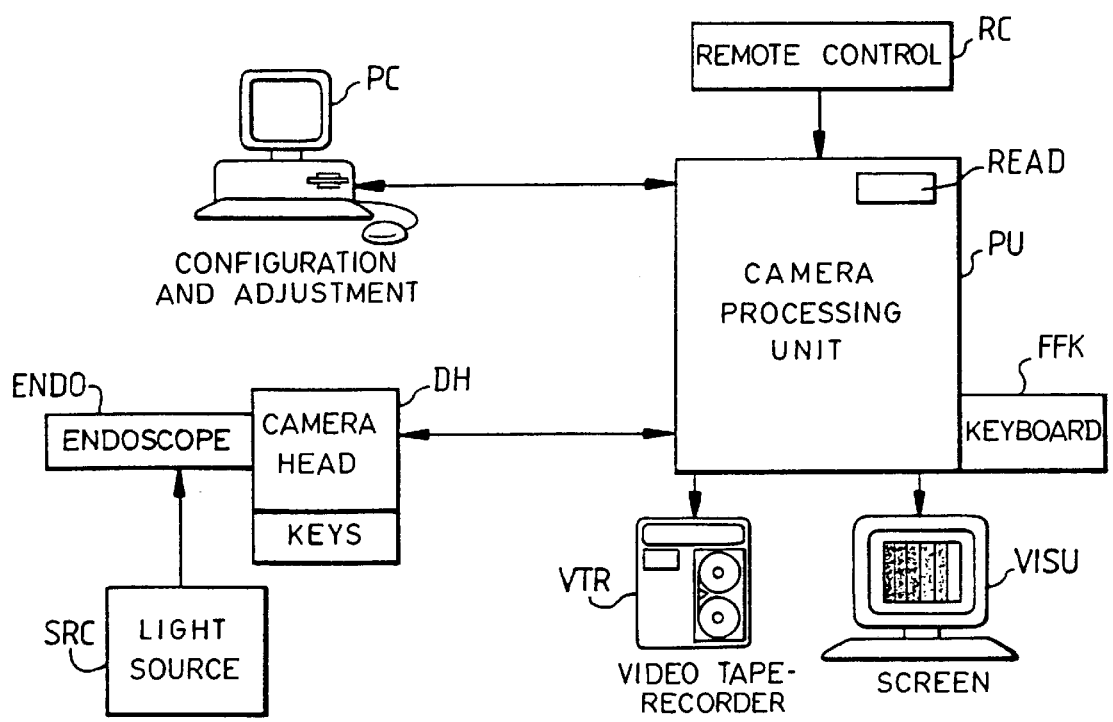
FIG. 1 shows an exemplary camera according to the invention.

FIG. 1 gives a schematic view of an exemplary digital camera according to the invention. This is an endoscopic camera consisting of a detection head DH comprising for example three CCD detectors (red, green, blue) equipped with setting keys, connected to an endoscope ENDO and linked to a processing unit PU. A light source SRC, also connected to the endoscope, provides the necessary illumination to observe the scene. The camera gives a color video to one or more screens VISU located in the operating room and enables the display of the images delivered by the camera. In this example, the processing unit is fitted out with a keyboard FFK positioned on its front face and with a chip-card reader READ. A remote control unit RC provided with keys is also connected to the processing unit PU. A video-tape recorder VTR is also provided for the recording of video images.

The digital camera comprises a plurality of setting parameters, very few of which are accessible in prior art endoscopic cameras. Indeed, it is not possible to propose all these settings to the user who, in this example, is a member of the hospital staff. For, he or she is not a specialist in the technique of cameras, and might lose precious time and put the camera out of order without being able to return to the desired configuration.

In the camera according to the invention, the processing unit PU contains a pre-set number of the prerecorded digital functions each enabling the setting of at least one parameter of the camera. A non-exhaustive list indicating examples of these functions is given in column 20 of the table of FIG. 2. In this example, there are setting functions 21 for the luminosity of the images delivered, colorimetry setting functions 22 and setting functions 23 relating to the quality of the images. Some of these functions make use of several parameters. For example, the automatic gain control (AGC) management function 211 acts on the AGC and the integration time of the CCD detectors to adapt the total gain of the camera to the luminosity of the observed scene. It may be note that if all these parameters are known in the technical field of cameras, they are mostly unknown to people who work with endoscopic cameras because, in the prior art cameras, they are set once and for all in the factory.

In the camera according to the invention, these functions are accessible by the user either directly or in the form of options combining a set of these functions. The column 24 of the table of FIG. 2 gives an indication, according to one example, of those functions that are directly accessible. In this case, it is the manual management of the gain (212), the management of the automatic gain control (211), the automatic balance of the white level (221), the manual balance of the white level (222). For these functions, specific keys are provided, for example on the front face keyboard FFK of the processing unit PU, or on the remote control RC, or again on the detection head DH of the camera. For the manual balance of the white levels (222), for example two keys "R' (red) and "B" (blue) accessible on the front face keyboard FFK or on the remote control make it possible to equalize the white levels, the level being possibly indicated by means of a light indicator on a bar comprising several levels. The accessibility by the user to certain functions can also be limited. For example, the manual gain management (212) may be limited to two gain values (for example 0 and 6 dB) when this function is directly called into operation by the user.

All these functions can also be accessible by the user in the form of options combining a set of these functions. These options are characteristic especially of a given environment and correspond to predetermined situations in which the camera may move. They therefore enable a non-specialist user of video techniques to have access through these options to all the setting parameters corresponding to these predetermined situations. The options are also pre-recorded in the processing unit PU.

FIG. 3 gives a view, in an exemplary endoscopic camera according to the invention, of the possible options for the user. These options are for example distributed under different menus. For example, the "Application" menu (311) contains operational application options (for example "abdominal", "thoracic", "neurosurgery", etc. depending on the type of surgical operation performed). The "Endoscope" menu (312) contains different options on the choice of the endoscope ENDO used. The "Ambience" menu (313) covers the significant options of the surgical or medical environment (for example "normal", "hemorrhagic", "hydric", "fat"). Each of these options makes use of a multitude of functions which themselves, when they are called into operation, lead to the settings of the corresponding parameters. The options are pre-recorded in a preliminary learning phase during tests performed under conditions of the operational situations corresponding to the different options. The options are accessible to the user, for example by means of four keys placed on the keyboard FFK on the front face of the processing unit and/or on the remote control. For example, a first key "MENU" provides access to the different menus. A key "VALID" validates the choice made. The other two keys symbolize for example arrows giving access to the different options of the menu. Thus the user, through the choice of the options that are most important to him and that directly pertain to the operational environment, can have access to all the setting parameters.

The processing unit of the camera according to the invention furthermore comprises a module for the initialization of the camera especially enabling the setting of the parameters of the camera in a standard configuration. When the user chooses one or more options, this defines a customized configuration different from a standard configuration pre-recorded in the processing unit. The user can then have the possibility of recording this configuration. A "configuration" menu accessible in the same way as the others enables him to make the choice from all the configurations, whether standard or customized.

When several users have to use the camera according to the invention, it is useful to customize certain setting functions, options or configurations used specifically by each, for example by means of a chip card proper to each user. This card may be read by the reader READ, the data register being managed in the same way as the others, by the processing unit.

In order to manage the data entered by the user, the processing unit PU comprises a module to monitor the data elements entered by the user. These data elements represent the functions and/or the options chosen. Certain data elements are considered as a matter of priority before the others. For example, the data entered by means of the keys of the detection head are given priority when considered. Between the data entered by the keyboard FFK and the data entered by the keys of the remote control unit RC, priority may be given to the data entered by means of the remote control unit.

The processing unit of the camera according to the invention also comprises a module to process the data that corresponds directly to functions or corresponds to options chosen by the user in order to make the corresponding settings of the camera. It may furthermore include a display module which, for each data element entered by the user, enables an overlay on the screen corresponding to this data element so that the user can view his or her choice. This possibility is particularly valuable when a large number of options is presented to the user. In particular, in the above example, the choice of the options in the menus can be done by displaying the different choices on the screen and validating the choice by means of the key "VALID". The processing unit may also comprise an additional pre-recorded function, herein called "STATUS", that the user can access by means of a specific key on the keyboard FFK, on the remote control or on the detection head. This function will enable the display on the screen, at any time, of the state of the settings as well as the configuration in progress.

The digital management of the setting functions is done for example by means of a microcontroller placed in the processing unit PU and controlling ASIC type integrated circuits enabling the processing in digital form of the video signals coming from the detection head of the camera.

Figure 4:
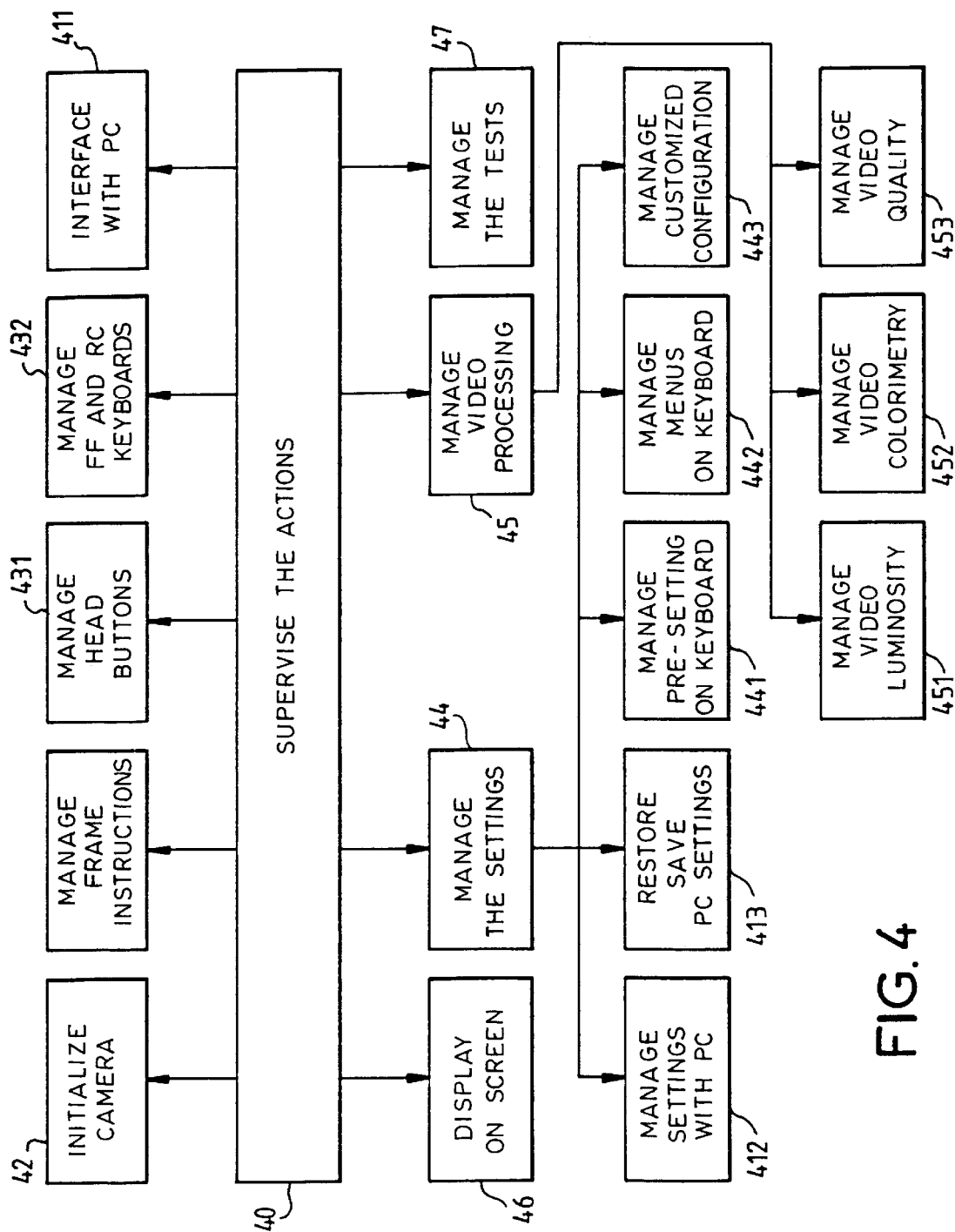
FIG. 4 shows the different steps of an exemplary implementation of the method according to the invention.

FIG. 4 summarizes the different steps of the method according to the invention in a particular example. It is implemented for example by means of a microcontroller that enables the supervision of all the actions (step 40).

It comprises a prior learning phase enabling the programming of the setting functions and options before an operational use of the camera. This programming can be done by means of a personal computer (PC in FIG. 1, and PC hereinafter) enabling the configuration of the microcontroller and a possible updating of data elements. In the example of FIG. 4, this learning phase corresponds to the step 411 of interfacing with the PC, the step 412 for the management of the settings with the PC (to test settings directly and prior to the use of the camera by a user) and the step 413 of restoration/saving with the PC. This step enables the recording of the setting functions and of the options.

When the processing unit is powered on by the user, the microcontroller acquires the hardware configuration in order to determine the mode of operation in progress. In particular, it detects whether the PC is connected (this is then a learning phase). In the operational phase (with the PC not connected), the method according to the invention comprises an initialization step 42. This step is used for example to detect whether the detection head is connected. When it is connected, the video processing of the camera and the setting of the parameters of the camera and the standard configuration are initialized.

The method of control according to the invention furthermore comprises the monitoring of the data entered by the user. In the example of FIG. 4, this comprises the step 431 for the management of the keys on the detection head and the step 432 for the management of the keyboard FFK on the front face and the keys of the remote control unit. It furthermore comprises the processing of these data elements which, as explained here above, correspond either directly to setting functions or to options chosen by the user. The processing of the data elements comprises the interpretation of the input data ("manage the settings" step 44); the "management of the pre-settings" step (441) corresponds to the setting functions that are directly called into operation, the "manage the menus" step (442) corresponds to the options called into operation by means of the menu. As referred to here above, a "manage the customized configuration" step (443) advantageously enables the calling into operation of one or more options chosen by the user and recorded in the form of a configuration. The processing of the data elements also comprises the management of the video processing operations (step 45) corresponding to the function called into operation. In the example referred to here above, these operations pertain to the management of the luminosity of the images acquired (step 451), the colorimetry (step 452) and the quality of the images (step 453).

According to this example, for each data element entered by the user, the method also comprises an overlay on the display screen corresponding to this data element, enabling the user to view his or her choice (step 45).

The control method according to the invention furthermore comprises other steps useful for imaging quality and standard digital camera control steps. For example, the "management of tests" (step 47) is used to validate the working of the camera by means of various video tests.

What is claimed is:

1. A method for digital control of a digital camera in a changing environment, the digital camera including a plurality of parameters, an optoelectrical detection head, and a processing unit connected to the optoelectrical detection head, the method comprising:

programming a pre-set number of digital setting functions recorded in the processing unit and a predetermined number of options that are characteristic of a given environment, wherein each of the digital setting functions is configured to enable setting of at least one parameter of the digital camera;

grouping together a set of the digital setting functions, the digital setting functions being accessible to at least one user either directly or by the options;

initializing the digital camera to enable the setting of the at least one parameter of the digital camera in a standard configuration;

monitoring data elements entered by the at least one user, the data elements representing at least one of the digital setting functions and the options chosen by the at least one user;

processing the data elements corresponding directly to setting the digital setting functions or the options chosen by the at least one user to carry out the corresponding settings of the digital camera; and customizing the setting of the at least one parameter of the digital camera automatically in a customized configuration for each of the at least one user based on the at least one of the digital setting functions and the options previously chosen by each of the at least one user, wherein a preliminary learning phase comprises the programming and the grouping, and the initializing, the customizing, the monitoring, and the processing occur when the processing unit is powered on by the at least one user.

2. The method according to claim 1, wherein the processing unit is connected to at least one screen configured to display images delivered by the digital camera, the processing unit comprises, for each data element entered by the at least one user, an overlay on the at least one screen corresponding to the data element that enables the at least one user to view a choice of configuration.

3. The method according to claim 2, wherein an additional function is accessible to the at least one user, the additional function enabling the display on the at least one display screen of a state of the settings corresponding to the digital setting functions and the additional function.

4. The method according to claim 1, further comprising:

a customized configuration management system enabling the at least one user, during the one or more options forming the customized configuration being chosen, to record the customized configuration in the processing unit.

5. The method according to claim 1, wherein the detection head enables acquisition of color images, and the digital setting functions enable setting of parameters of the at least one parameter linked to luminosity, colorimetry, and quality of the images delivered by the digital camera.

6. A method for digital control of an endoscopic camera, the endoscopic camera including a plurality of parameters, an optoelectrical detection head connected to an endoscope configured to be introduced into a patient body during a surgical operation, and a processing unit connected to the optoelectrical detection head, the method comprising:

programming a pre-set number of digital setting functions recorded in the processing unit and a predetermined number of options that are characteristic of situations of surgical operations, wherein each of the digital setting functions is configured to enable setting of at least one parameter of the endoscopic camera;

grouping together a set of the digital setting functions, the digital setting functions being accessible to at least one user either directly or by the options;

initializing the endoscopic camera enabling the setting of the at least one parameter of the endoscopic camera in a standard configuration;

monitoring data elements entered by the at least one user, the data elements representing at least one of the digital setting functions and the options chosen by the at least one user;

processing the data elements corresponding directly to the digital setting functions or the options chosen by the at least one user to carry out corresponding settings of the endoscopic camera; and customizing the setting of the at least one parameter of the endoscopic camera automatically in a customized configuration for each of the at least one user based on the at least one of the digital setting functions and the options previously chosen by each of the at least one user, wherein a preliminary learning phase comprises the programming and the grouping, and the initializing, the customizing, the monitoring, and the processing occur when the processing unit is powered on by the at least one user.

7. The method according to claim 6, wherein the options are distributed into menus that include at least one of an operational application, a type of endoscope used, a choice of a source, and an environment in which the surgical operation takes place.

8. A digital camera for display in a changing environment, the digital camera including a plurality of settings, an optoelectrical detection head, and a processing unit connected to the detection head, wherein the processing unit comprises:

a preset number of pre-recorded digital setting functions and a predetermined number of options that are characteristic of a given environment, each of the pre-recorded digital setting functions enabling setting of at least one parameter of the digital camera;

a module configured to group together a set of the pre-recorded digital setting functions, the pre-recorded digital setting functions being accessible to at least one user either directly or by the options;

a module configured to initialize the digital camera enabling the setting of the at least one parameter of the digital camera in a standard configuration;

a module configured to monitor data elements entered by the at least one user, the data elements representing at least one of the pre-recorded digital setting functions and the options chosen by the at least one user;

a module configured to process the data elements corresponding directly to the pre-recorded digital setting functions or the options chosen by the at least one user to carry out corresponding settings of the digital camera; and a module configured to customize the setting of the at least one parameter of the digital camera automatically in a customized configuration for each of the at least one user based on the at least one of the digital setting functions and the options previously chosen by each of the at least one user.

9. The camera according to claim 8, wherein the data elements are entered by the at least one user using a keyboard positioned on a front face of the processing unit.

10. The camera according to claim 8, wherein the data elements are entered by the at least one user using keys accessible on a remote control unit.

11. The camera according to claim 8, wherein the data elements are entered by the at least one user using buttons accessible on the detection head of the digital camera, the data elements entered using the buttons being processed as a priority over the data elements entered by other means.

12. The camera according to claim 8, wherein the processing unit is equipped with a chip-card reader configured to enable customized data elements to be entered for a particular user at least one user using a chip card introduced into the chip-card reader, wherein the customized data elements are used to configure the customized configuration.

13. The camera according to claim 8, wherein, the processing unit is connected to at least one screen for the display of images delivered by the digital camera, and wherein the processing unit includes a display module enabling, for each of the data elements entered by the at least one user, an overlay on the at least one screen corresponding to the data elements and enabling the at least one user to view a choice of configuration.

14. The camera according to claim 13, wherein the data elements are entered by the at least one user using a keyboard positioned on a front face of the processing unit.

15. The camera according to claim 13, wherein the data elements are entered by the at least one user using keys accessible on a remote control unit.

16. The camera according to claim 13, wherein the data elements are entered by the at least one user using buttons accessible on the detection head of the digital camera, the data elements entered using the buttons being processed as a priority over the data elements entered by other means.

17. The camera according to claim 13, wherein the processing unit is equipped with a chip-card reader configured to enable customized data elements to be entered for a particular user of the at least one user using a chip card introduced into the chip-card reader, wherein the customized data elements are used to configure the customized configuration.

18. An endoscopic camera, the endoscopic camera including a plurality of settings, an optoelectrical detection head connected to an endoscope that can be introduced into a patient body during a surgical operation, and a processing unit connected to the optoelectrical detection head, wherein the processing unit comprises:

a pre-set number of pre-recorded digital setting functions and a predetermined number of options that are characteristic of a given environment, each of the pre-recorded digital setting functions enabling setting of at least one parameter of the endoscopic camera;

a module configured to group together a set of the pre-recorded digital setting functions, the pre-recorded digital setting functions being accessible to at least one user either directly or by the options;

a module configured to initialize the endoscopic camera enabling the setting of the at least one parameter of the camera in a standard configuration;

a module configured to monitor data elements entered by the at least one user, the data elements representing at least one of the pre-recorded digital setting functions and the options chosen by the at least one user;

a module configured to process the data elements corresponding directly to the at least one of the pre-recorded digital setting functions and the options chosen by the at least one user to carry out corresponding settings of the endoscopic camera; and a module configured to customize the setting of the at least one parameter of the endoscopic camera automatically in a customized configuration for each of the at least one user based on the at least one of the digital setting functions and the options previously chosen by each of the at least one user.

19. The camera according to claim 18, wherein the options are distributed into menus that include at least one of an operational application, a type of endoscope used, a choice of a source, and an environment of the surgical operation.

* * * * *